(12) United States Patent
Smalyukh et al.

(10) Patent No.: US 12,384,899 B2
(45) Date of Patent: Aug. 12, 2025

(54) CELLULOSIC GELS, FILMS AND COMPOSITES INCLUDING THE GELS, AND METHODS OF FORMING SAME

(71) Applicant: The Regents of the University of Colorado, Denver, CO (US)

(72) Inventors: Ivan I. Smalyukh, Boulder, CO (US); Andrew Johnston Hess, Louisville, CO (US); Quingkun Liu, Boulder, CO (US); Joshua A De La Cruz, Denver, CO (US); Blaise Fleury, Boulder, CO (US); Eldho Abraham, Boulder, CO (US); Bohdan Senyuk, Boulder, CO (US); Vladyslav Cherpak, Westminster, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 18/603,094

(22) Filed: Mar. 12, 2024

(65) Prior Publication Data
US 2024/0218144 A1    Jul. 4, 2024

Related U.S. Application Data

(63) Continuation of application No. 17/251,694, filed as application No. PCT/US2019/037123 on Jun. 13, 2019, now Pat. No. 11,999,836.

(60) Provisional application No. 62/684,670, filed on Jun. 13, 2018.

(51) Int. Cl.
| C08J 9/28 | (2006.01) |
| C08J 5/18 | (2006.01) |
| C08K 5/544 | (2006.01) |
| C08K 7/02 | (2006.01) |

(Continued)

(52) U.S. Cl.
CPC .  *C08J 9/28* (2013.01); *C08J 5/18* (2013.01); *C08K 5/544* (2013.01); *C08K 7/02* (2013.01); *B82Y 30/00* (2013.01); *B82Y 40/00* (2013.01); *C08J 2201/026* (2013.01); *C08J 2201/0504* (2013.01); *C08J 2205/026* (2013.01);
(Continued)

(58) Field of Classification Search
CPC . C08J 9/28; C08J 5/18; C08J 2201/026; C08J 2201/0504; C08J 2205/026; C08J 2205/028; C08J 2301/02; C08J 2201/011; C08J 3/24; C08J 2301/10; C08K 5/544; C08K 7/02; B82Y 30/00; B82Y 40/00; C08B 3/14; C08B 15/005; C08B 15/04; C08F 130/08; C08L 1/10; C12P 19/04
See application file for complete search history.

(56) References Cited

U.S. PATENT DOCUMENTS

| 2007/0259169 A1* | 11/2007 | Williams | C08J 5/04 428/323 |
| 2011/0021671 A1* | 1/2011 | Kuga | C08J 9/28 524/35 |

FOREIGN PATENT DOCUMENTS

JP    2017115047 A  *  6/2017

\* cited by examiner

*Primary Examiner* — K. Boyle
(74) *Attorney, Agent, or Firm* — Snell & Wilmer L.L.P.

(57) ABSTRACT

Disclosed are cellulose-based flexible aerogels and xerogels containing bacterial cellulose nanorods, ribbons, fibers, and the like, wherein the gels have tunable optical, heat transfer, and stiffness properties. Further disclosed are highly transparent and flexible cellulose nanofiber-polysiloxane composite aerogels featuring enhanced mechanical robustness, tunable optical anisotropy, and low thermal conductivity.

7 Claims, 16 Drawing Sheets

(51) Int. Cl.
*B82Y 30/00* (2011.01)
*B82Y 40/00* (2011.01)
(52) U.S. Cl.
CPC ...... *C08J 2205/028* (2013.01); *C08J 2301/02* (2013.01); *C08K 2201/011* (2013.01)

Hydrogel attached to the glass

Side view

CELLULOSIC GELS, FILMS AND COMPOSITES INCLUDING THE GELS, AND METHODS OF FORMING SAME

CROSS-REFERENCE TO RELATED APPLICATIONS

This application is a continuation of U.S. National Stage application Ser. No. 17/251,694, entitled CELLULOSIC GELS, FILMS AND COMPOSITES INCLUDING THE GELS, AND METHODS OF FORMING SAME, and filed Dec. 11, 2020, which is the national stage entry of International Application No. PCT/US19/37123, entitled CELLULOSIC GELS, FILMS AND COMPOSITES INCLUDING THE GELS, AND METHODS OF FORMING SAME, and filed Jun. 13, 2019, and claims the benefit of U.S. Provisional Application No. 62/684,670, entitled PROCESS FOR PREPARING NANOCELLULOSE XEROGELS, and filed Jun. 13, 2018, the contents of which are hereby incorporated herein by reference to the extent that such contents do not conflict with the present disclosure.

FEDERALLY-SPONSORED RESEARCH

This invention was made with government support under Award No. DE-AR0000743 awarded by the U.S. Department of Energy and under grant DMR-1410735 awarded by the U.S. National Science Foundation. The government has certain rights in the invention.

FIELD

The disclosure relates to cellulose-based gels, such as (e.g., flexible) aerogels and xerogels. Exemplary cellulose-based gels include cellulose nanorods, ribbons, fibers, and the like, wherein the gels can have tunable properties, such as optical, thermal, and mechanical properties. Further disclosed are highly transparent and flexible cellulose nanofiber-polysiloxane composite aerogels featuring enhanced mechanical properties, such as robustness, tunable optical anisotropy, and low thermal conductivity.

BRIEF DESCRIPTION OF THE FIGURES

FIG. 1A shows the gel before solvent exchange with isopropyl alcohol FIG. 1B shows after the alcogel in the first eight hours with isopropyl alcohol, FIG. 1C shows the shrinking behavior of the alcogel during the second 8 hour exchange with isopropyl alcohol, FIG. 1D shows that the alcogel springs back to become transparent in third 8 hour of exchange with isopropyl alcohol, and FIG. 1E shows the final polyvinylmethyldimethyoxysilyl (PVMDMS) ambient-dried aerogel.

FIG. 3A shows WBW after autoclave treatment in the culture chamber, FIG. 3B after two week and FIG. 3C pellicle taken out for purification.

FIG. 4A shows material treated with 1% NaOH at 80° C., FIG. 4B depicts material treated with DI water and FIG. 4C shows the final purified bacterial cellulose.

FIG. 6A shows the mold for the polycondensation reaction chamber made of glass, FIG. 6B the organogel fabrication setup in water bath heating, FIG. 6C the organogel in DI water, FIG. 6D the organogel in water/isopropanol, FIG. 6E the organogel in isopropanol and FIG. 6F shows the final aerogel.

DETAILED DESCRIPTION

Figure 1A:
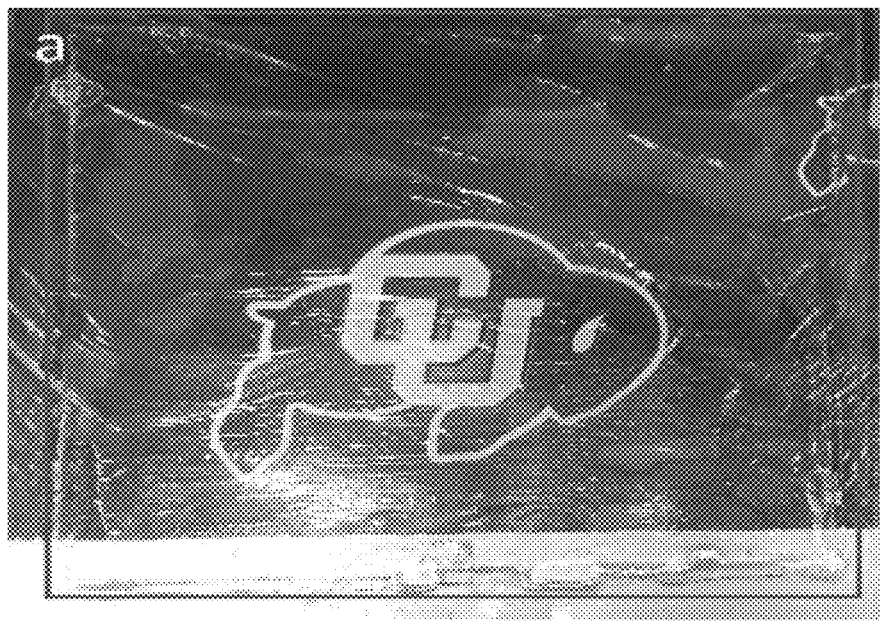
FIGS. 1A-1E depict the transparency characteristics during the course of a disclosed xerogel formation.

As used herein, a "gel" is understood to be a substantially dilute cross-linked system that exhibits no flow when in the steady state. The primary constituent of the gel is the ambient fluid surrounding it, whose form can be a liquid or gas. Prefixes such as "aero," "organo," "hydro," and variations are understood to indicate the ambient fluid in the cross-linked gel matrix and primary component of the gel material.

The disclosed gels can contain cellulosic nanocomposites that can be aligned liquid crystal phases. As such, the disclosed gels allow the formulator to adjust the optical transmissivity of the gel, thereby configuring the optical properties of the gel to range from opaque to transparent. In addition, the properties can be adjusted to interact with a wide range of the electromagnetic radiation, for example, from the visible spectrum to infrared spectrum. In one embodiment, the thermal conductivity of the gel can be adjusted. The bulk properties of the disclosed gels, for example the level of stiffness or flexibility can be adjusted by the choice of the constituent cellulosic material, for example, nanorods, ribbons, fibers, and the like, as well as, the concentration of these materials in the resulting gels.

As used herein, a "film" and variations indicate lamellae that can range in thickness from, for example, about from about 1 µm to about 10 cm or from about 10 nm to 1 mm and arbitrary lateral extent.

As used herein the term "cross-section" means width and the terms are used interchangeably. The disclosed cellulosic nanomaterials have a width from about 10 nm to about 500 nm or less than 1 nm or even below 0.1 nm. The length of the nanomaterials can be at least or less than ten times the width.

The term "composition" as used herein can refer to the disclosed cellulose nanomaterial aqueous dispersions, hydrogels, organogels, aerogels, and liquid crystal gels. The compositions can be a single layer of material comprising nanomaterials or the composition can be formed from two or more distinct layers wherein each layer consists of only one material. As a non-limiting example, one layer can consist of an ordered nematic cellulosic gel onto which a second layer of aligned cholesteric cellulose film is applied thereto. This layering thereby forms a unified composite material with distinct layers.

The term "hydrogel" as used herein represents a network of cellulosic material as a colloidal gel dispersed in a carrier. In one embodiment the carrier is water. In another embodiment the carrier is a mixture of a water compatible (miscible) organic solvent. The cellulosic material can be cross-linked or non-crosslinked.

The term "xerogel" is defined herein as a gel whose principal solvent is ambient gas, such as air, and whose liquid-gas solvent exchange is accomplished via evaporation of the liquid in atmospheric conditions near that of ambient temperature and pressure.

The term "nanomaterial" refers to the disclosed cellulosic material. The width of these materials is in the nanometer range, whereas the length of the cellulosic material can vary from nanometer length to micrometer. The terms "nanomaterial," "cellulosic material" and "cellulosic nanomaterial" are used interchangeably throughout the present disclosure.

Disclosed herein are processes for forming gels, such as xerogels and aerogels. Exemplary xerogels comprise nanocellulose constituents having liquid crystal ordering in the xerogel's polymer skeletal structure.

Further exemplary bacterial cellulose-based flexible gels can comprise cellulose ribbons, fibers, and other constituent-particle structures having in one embodiment aspect ratios of about 1:1000. These flexible gels can be formed from linking the cellulose particle networks within the material. The original cellulose solvent that is used for the formation of a gel network can be retained or replaced to yield a variety of gel types, for example, hydrogels, alcogels, aerogels, and liquid-crystal gels. The use of the disclosed cellulosic material to form the gel network allows the formulator to adjust various properties of the gels, including the flexibility of the gels.

In addition to flexibility, the optical transmissivity of the disclosed gels can be adjusted to range from opaque to transparent. These results can be obtained by adjusting the various properties of the disclosed composites, i.e., density of cellulosic nanomaterial or size distribution. Also, the addition of adjunct ingredients such as liquid crystal materials can be used to tune the optical properties of the disclosed composites.

A further property which can be tailored is the degree of thermal resistance displayed by the gels. Several factors enable the adjustment of the thermal resistive properties, including: (1) the intrinsically low thermal conductivity of cellulose, (2) the rarefication of fluid within the cellulose network thereby regulating the thermal convection, and (3) the thermal conductivity and convection properties of the fluids which comprise the cellulose-gel network.

In another aspect of the present disclosure are compositions comprising cellulosic nanorods that are aligned and which orientation can be adjusted by the formulator. The disclosed nanorods can have aspect ratios from about 1:10 to about 1:100. In one aspect, the disclosed nanorods can be used to form compositions with a cholesteric phase.

In one embodiment the disclosed nanocrystals form ordered films that can be ordered into a cholesteric phase in the film to form a periodic structure whose pitch and pitch gradient are adjustable for broad-band Bragg reflection of incident electromagnetic radiation. In another embodiment the resulting ordered gels are obtained because of the small relative aspect ratios of the cellulose nanorods or similar nanomaterials that comprise the nanocrystals. Nanorods result in the formation of different phases than other nanomaterials, such as nanofibers. Because of this fact broad-band reflection is enabled in ordered cellulose gels that are formed from cellulose structures with aspect ratios of, for example, about 1:10 to about 1:100.

As such, the mechanical flexibility, optical transmissivity, and thermal resistance can be configured by tuning—e.g., the same parameters described above in connection nanofibers, except that those parameters now refer specifically to cellulose nanorods or other geometrically anisotropic cellulose structures.

A further aspect of the present disclosure relates to composite structures comprising lamellae that are formed from the disclosed aerogels and/or liquid crystal gels. Composite structures with lamellae can be formed from the disclosed compositions that comprise nanofiber-like cellulosic materials (e.g., to form nematic phase material) or from nanorod-like cellulosic materials (e.g., to form cholesteric phase material). These composite structures comprise a plurality of layers.

The disclosed gels and/or films can have a thickness from about 1 μm to about 10 cm. In one embodiment the thickness varies from about 10 μm to about 1 cm. In another embodiment the thickness varies from about 100 μm to about 10 cm. In a further embodiment the thickness varies from about 50 μm to about 1 cm. In still further embodiment the thickness varies from about 1 cm to about 10 cm. In a yet another embodiment the thickness varies from about 10 μm to about 100 cm. In a yet still further embodiment the thickness varies from about 500 μm to about 10 cm.

The transmissivity of the disclosed gels and/or films relates to the amount of visible electromagnetic radiation that passes through the gel. 0% transmission results in an opaque material which allows no transmission. 100% transmission results in a material that is transparent to electromagnetic radiation. The disclosed gels can have a transmission of from 0% to 100%. In one embodiment the gels have a transmission of from about 5% to about 15%. In another embodiment the gels have a transmission of from about 25% to about 50%. In a further embodiment the gels have a transmission of from about 95% to about 100%. In a still further embodiment the gels have a transmission of from about 15% to about 35%. In a yet further embodiment the gels have a transmission of from about 50% to about 75%. In a yet another embodiment the gels have a transmission of from about 25% to about 75%. By way of particular examples, the gels and/or films exhibit an electromagnetic transmission of from 0% to 100%, or about 25% to about 100% for light wavelengths between about 400 nm and about 700 nm.

The disclosed gels and composite materials can have a thermal conductivity of from about $10^{-3}$ W/(m·K) to about 10 W/(m·K). In another embodiment the thermal conductivity is from about $10^{-2}$ W/(m·K) to about 10 W/(m·K). In a further embodiment the thermal conductivity is from about $10^{-1}$ W/(m·K) to about 10 W/(m·K). In a still further embodiment the thermal conductivity is from about $10^{-3}$ W/(m·K) to about 1 W/(m·K). In yet further embodiment the thermal conductivity is from about $10^{-2}$ W/(m·K) to about 1

W/(m·K). In yet another embodiment the thermal conductivity is from about 1 W/(m·K) to about 10 W/(m·K).

The relative emissivity value of the disclosed gels ranges from about $10^{-2}$ to 0.99.

The disclosed gels and composites can have a bulk modulus of from about 1 Pa to about $10^6$ Pa. In one embodiment the modulus is from about 10 Pa to about $10^5$ Pa. In another embodiment the modulus is from about $10^2$ Pa to about $10^6$ Pa. In a further embodiment the modulus is from about $10^3$ Pa to about $10^5$ Pa. In a still further embodiment the modulus is from about 10 Pa to about $10^3$ Pa. In a yet further embodiment the modulus is from about 1 Pa to about 10 Pa. In a yet another embodiment the modulus is from about $10^4$ Pa to about $10^6$ Pa.

In accordance with various embodiments of the disclosure, a process for preparing a gel includes:
 a) oxidizing alcohol units of bacterial cellulose to form bacterial cellulose containing a plurality of carboxylate groups and/or carboxylic acid groups;
 b) reacting the oxidized bacterial cellulose carboxylate groups with a surface modifying agent to form surface modified bacterial cellulose; and
 c) reacting in a solvent the surface modified bacterial cellulose with a crosslinking agent to form a bacterial cellulose aerogel.

The process can additionally include exchanging the aqueous solution present in the gel with a solvent and/or removing by drying the volatile solvent to form a xerogel. The bacterial cellulose if obtained from, for example, one or more of *Acetobacter hansenii* and *Acetobacter xylinum*. The crosslinking agent comprises a polysiloxane precursor, such as one or more of vinylmethyldimethoxysilane, methyltrimethoxysilane, and methyltriethoxysilane. The surface modifying agent comprises a compound comprising an amine functional group and a silicon atom, such as one or more of a silylamine or one or more aminoalkylsilanes. A gel or film can be formed according to this method or other methods described herein.

In accordance with further exemplary embodiments, a process for preparing networked cellulosic aerogels includes the steps of:
 a) contacting a dispersion of bacterial cellulose with an oxidizing system that oxidizes hydroxyl units of cellulose to carboxylate and/or carboxylic acid units to form a solution of oxidized cellulose nanofibers;
 b) reacting the oxidized cellulose nanofibers with a surface modifying agent to form a solution of surface modified cellulose nanofibers;
 c) contacting the surface modified cellulose nanofibers with a crosslinking agent to form a bacterial cellulose nanofiber matrix;
 d) hydrolyzing the matrix in the presence of a catalyst to form networked cellulosic hydrogel;
 e) exchanging solvent contained in the hydrogel with a volatile solvent to form an organogel; and
 f) removing the solvent to form an aerogel.

The bacterial cellulose can be obtained from one or more of *Acetobacter hansenii* and *Acetobacter xylinum*. The surface modified cellulose nanofibers can be modified by a compound chosen from a C1-C6 linear or branched, saturated or unsaturated alkylamine, a low molecular weight compound comprising a cationic moiety, oligomers and/or polymers and/or other modifying agents described herein, such as a compound comprising allylamine.

Also disclosed is a method for preparing gels, such as transparent hydrogels, comprising:
 a) oxidizing (e.g., primary) alcohol units of bacterial cellulose to form bacterial cellulose containing a plurality of carboxylate groups and/or carboxylic acid groups;
 b) reacting the oxidized bacterial cellulose carboxylate and/or carboxylic acid groups with a surface modifying agent to form surface modified bacterial cellulose; and
 c) reacting the surface modified bacterial cellulose with a (e.g., silyl) crosslinking agent to form a bacterial cellulose aerogel.

One aspect relates to oxidizing the bacterial cellulose in step (a) with sodium hypochlorite in the presence of 2,2,6,6-tetramethylpiperidine-1-oxyl (TEMPO).

A further aspect relates to the use of aminopropyltrimethoxysilane or other suitable agent as the surface modifying agent in step (b). As used through this disclosure, a surface modifying agent can include a compound comprising an amine functional group and a silicon atom, such as silylamine or one or more aminoalkylsilanes.

Another aspect relates to the use of trimethoxymethylsilane or other polysiloxane precursor as the crosslinking agent in step (c).

Further disclosed is a method for preparing transparent xerogels, comprising:
 a) oxidizing (e.g., primary) alcohol units of bacterial cellulose to form bacterial cellulose containing a plurality of carboxylate groups and/or carboxylic acid groups;
 b) reacting the oxidized bacterial cellulose carboxylate groups and/or carboxylic acid with a surface modifying agent to form surface modified bacterial cellulose;
 c) reacting in a solvent, such as water, the surface modified bacterial cellulose with a (e.g., silyl) crosslinking agent to form a bacterial cellulose aerogel;
 d) exchanging the solvent present in the aerogel with a solvent; and
 e) removing by drying the volatile solvent to form a xerogel.

Still further disclosed herein is a process for preparing networked cellulosic aerogels, comprising:
 a) contacting an aqueous dispersion of bacterial cellulose with an oxidizing system that oxidizes (e.g., C6 hydroxyl units) of cellulose to carboxylate units and/or carboxylic acid to form an aqueous solution of oxidized cellulose nanofibers;
 b) reacting the oxidized cellulose nanofibers with a surface modifying agent to form an aqueous solution of surface modified cellulose nanofibers;
 c) contacting the surface modified cellulose nanofibers with a reagent (e.g., polyvinylmethyl-siloxane (PVMS)) to form a polysiloxane precursor;
 d) hydrolyzing the polysiloxane precursor in the presence of an acid catalyst to form a PMSQ network cellulosic hydrogel;
 e) exchanging the solvent contained in the hydrogel with a solvent to form an organogel; and
 f) removing the solvent to form an aerogel.

Disclosed herein is a process for preparing xerogels. Exemplary processes are based on consecutive processes involving radical polymerization and hydrolytic polycondensation, followed by ultralow-cost, highly scalable, ambient-pressure drying directly from alcohol as a drying medium without any modification or additional solvent exchange. Polyvinylpoly-methylsiloxane, $(CH_2CH(Si(CH_3)O))_n$, a flexible polymer can be used as a crosslinker for the ambient-dried cellulose aerogel. This polymer is formed by reacting the surface modified bacterial cellulose with vinylmethyldimethoxysilane or other suitable agent. As used throughout this disclosure, a crosslinking agent can comprise a polysiloxane precursor, such as one or more of vinylmethyldimethoxysilane, methyltrimethoxysilane, and methyltriethoxysilane.

Radical polymerization of monomers that contain alkene groups is an effective approach to enhance the mechanical properties of ambient-dried aerogel. Radical polymerization of vinyl groups in the network of polyvinylsilsesquioxane gels together with silane modified CNF also leads to mechanically reinforced xerogels. Flexible hybrid wet gels and dense gel films can be obtained by radical polymerization of VTMS, followed by hydrolytic polycondensation. In PVMDMS, the polyethylene chains interconnected with siloxane bonds and CNF-APTMS dispersed in the network provide flexibility to the hybrid gel. In addition, mechanically strong and flexible organic polymer hydrogels with a double network structure were synthesized via radical polymerization.

The resulting ambient-dried aerogels show a homogeneous, tunable, highly porous, doubly cross-linked nanostructure with the elastic polymethylsiloxane network cross-linked with flexible hydrocarbon chains and functionalized cellulose nanofibers (CNF-APTMS). The disclosed process results in an ultralow cost, high scalability, uniform pore size, high surface area, high transparency, high hydrophobicity, excellent machinability, superflexibility in compression, superflexibility in bending, and superinsulating properties could be achieved in a single ambient-dried aerogels.

In one aspect disclosed herein is an intermediate-scale cellulose-polysiloxane aerogel prepared using a critical point drying method. For example, aerogels of 6.5-inch diameters were prepared by crosslinking quaternary amine-capped cellulose nanofibers in polysiloxane network. Aerogel formed using CNF-APTMS shows excellent optical transparency, thermal insulation and flexibility. The cellulose aerogel has a 99% of transmission, 2% of haze. The color rendering index of this aerogel is 0.99. The aerogel has a low thermal conductivity of 11 mW/K/m and a thermal conductance less than 7.3 W/K/m$^2$.

Feedstock

Disclosed herein are readily available feedstocks that are useful for preparing the disclosed gels. In one non-limiting example, bacterial cellulose derived from *Acetobacter hansenii* in the beer wort waste was used. There are plenty of carbohydrates and amino acids in beer wort waste, which is ideal cultural solution for producing bacterial cellulose. To provide a suitable culture media 1% glucose was added to beer wort which provided a suitable yield of bacterial cellulose as a low cost alternative to standard media.

The use of waste beer wort and/or waste beer (WBW) for the large-scale production of bacterial cellulose (BC) by bulk and the effect of unwanted contaminates found in the feedstock has been previously studied. The BC generated was used for the production of transparent flexible siloxane aerogel (critical pressure dried with liquid CO2) and xerogel (ambient pressure dried) useful for window insulating applications.

Beer production is an important economic activity in USA and hence thousands of gallons waste beer wort is generating in each brewery every year. Being the major by-product from brewing industry after spent grain which is for livestock and fowl, WBW is thrown away in the drainage that creates enormous waste and series of environmental problems. WBW mainly composed of 48-55% protein, 23-28% carbohydrate, 6-8% RNA, 1% glutathione, and 2% vitamin B. Moreover, they are rich in elements like P, K, Ca, Fe, P and Mg. Because of this high nutritional content, it might be used as a nutrient source for microorganisms. To use these carbohydrates and proteins directly by microorganisms as a nutrient source, a pre-treatment may be desired to depolymerize large polysaccharide molecules since most of the protein and carbohydrate exists in the cell walls in the form of large polymers.

Because monosaccharides can be used by *Acetobacter hansenii* to produce bacterial cellulose, cutting down the large polysaccharide molecules is desirable to use it as a nutrient source. A one step pre-treatment, namely thermochemical high temp and pressure autoclaving in a mild acidic atmosphere could be effective for this purpose. This process should be not only effective for disrupting cells and dispersing large polymer aggregates, but also for improving hydrolysis. In previous reports, waste beer yeast cells have been used for the production of bioethanol by the releasing the nutrients through chemical pre-treatments including acid hydrolysis, alkali hydrolysis and enzymatic hydrolysis.1 For the production of BC, WBW collected from local breweries was treated with an autoclave treatment (thermo-chemical) for 45 min at 120° C. and 50 pounds per square inch pressure. After this thermo-chemical treatment, a high-speed homogenizer followed by a chemical treatment with 1M NaOH and make the WBW pH at 5.5 is necessary to make it suitable for bacterial growth.

After autoclaving pre-treatment with mild acidic condition, WBW was homogenized and centrifuged at 4000 g for 15 min to remove sediments and the supernatant was collected and added with sterilized glucose solution (50%, w/v) to reach a final concentration of 1% (w/v).

WBW hydrolysates prepared as described above then treated with 1M NaOH for adjusting its pH to 5.5. Finally, the prepared *Acetobacter hansenii* culture inoculum was transferred (5%, w/v) into the glass dishes (2000 mL) containing 1500 mL of WBW culture and they were cultivated statically at 26° C. for 14-21 days.

After hydrolysis, *Acetobacter hansenii* were directly supplied to WBW hydrolysates as carbon and nutrient sources to produce BC. Although some researchers have investigated various cellulosic wastes from renewable forestry residues or industrial by-products to produce BC, some extra nutrients are added to media to improve the BC yield. This could be likely due to the fact that the un-centrifuged samples after these pre-treatments have a high sugar concentration (they showed the highest sugar yields) which could cause the inhibition of the BC production and reduce the supply of oxygen by the liquid medium. While in the centrifuged samples the reducing sugar concentration was decreased by diluting the supernatant with water, which could lead to a better concentration for BC production. Likely the cellulose production by *Acetobacter hansenii* in this case was inhibited due to the low sugar concentration present in the centrifuged samples, which were further diluted from the already low sugar yields of WBW obtained from these pre-treatments. Therefore, we supplied 1% sugar to the WBW culture.

Figure 3A:
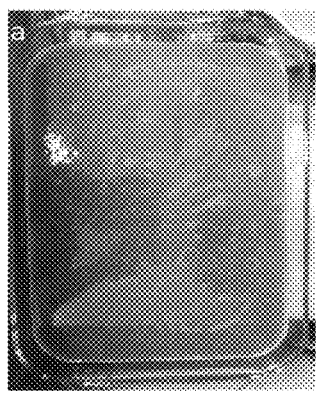
FIGS. 3A-3C depict the bacterial cellulose pellicle obtained from beer wort.
Figure 3B:
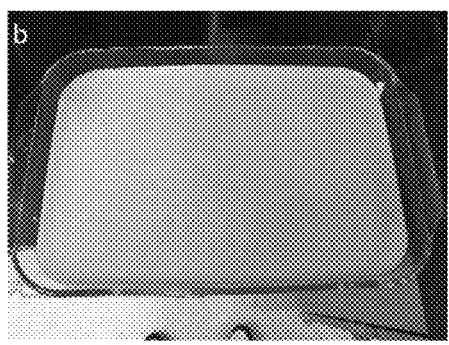
Figure 3C:
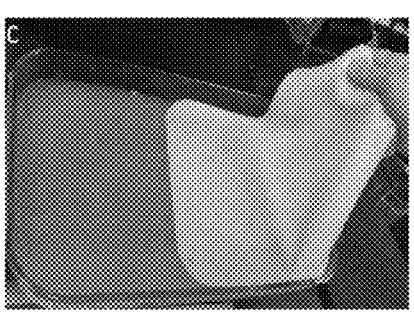
Figures 4A, 4B, 4C:
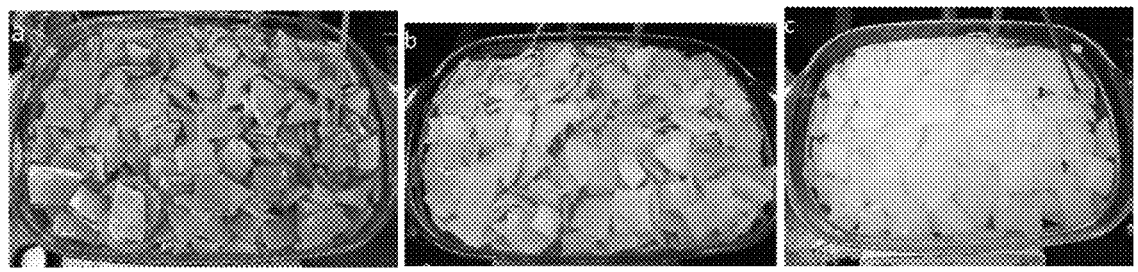
FIGS. 4A-4C show the bacterial cellulose pellicles at different stages of purification.

BC pellicles with 10-14 mm thickness were successfully produced with pre-treated WBW culture media as depicted in FIGS. 3A-3C. FIG. 3A shows WBW after autoclave treatment in the culture chamber, FIG. 3B after two week and FIG. 3C pellicle taken out for purification. After cultivation, the BC membranes were rinsed with running water overnight, soaked in 1 M NaOH at 80° C. for 2 hours to remove bacteria, and then washed with deionized water several times to completely remove alkali. FIGS. 4A-4C show the pellicles at different stages of purification. FIG. 4A shows material treated with 1% NaOH at 80° C., FIG. 4B depicts material treated with DI water and FIG. 4C shows the final purified BC. The pellicles were stored in closed containers with DI water as the solvent for further analysis, applications and TEMPO oxidations. BC production using WBW displayed a comparable yield with conventionally used chemical media.

Oxidation of Bacterial Cellulose

In order to provide the desired carboxylate groups and/or carboxylic acid groups for crosslinking the bacterial cellulose is oxidized using, for example, sodium hypochlorite and catalytic amounts of 2,2,6,6-tetramethylpiperidine-1-oxyl (TEMPO) radical at pH 10 in water. For example, 2 g of bacterial cellulose was suspended in water (150 mL) containing TEMPO (0.025 g) and NaBr (0.25 g). A 1.8 M NaClO solution (4 mL) was added, and the pH of the suspension was maintained at 10 by adding 0.5 M NaOH. When no more decrease in pH was observed, the reaction was finished. The pH is then adjusted to 7 by adding 0.5M HCl. The TEMPO-oxidized products were cellulose nanorods of controlled 4-10 nm diameter and 1000-3000 nm length, which were then thoroughly washed with water by filtration and stored at 4° C. The produced CNF—COOH is transparent and highly viscous material in aqueous dispersion.

Figure 11:
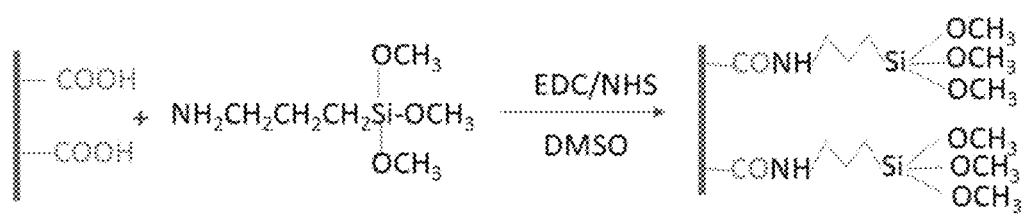
FIG. 11 illustrates a procedure in accordance with at least one embodiment of the disclosure.

The chemical modification of CNFs with silanes provides a versatile route for structural and property design suitable for polysiloxane coupling reactions. The BC successfully produced by the low-cost method has been oxidized with TEMPO mediated oxidation and eventually received transparent carboxylated CNF aqueous dispersions with 0.2 wt. %. Due to the chemical functionality of CNFs bearing hydroxyl and carboxylic acid groups, amidation with amine silanes will be a suitable method. Using this method carboxylate groups were selectively activated on each cellulose molecules with a water-soluble carbodiimide EDC·HCl [N-(3-dimethylaminopropyl)-N'-ethylcarbodiimide hydrochloride)] and N-hydroxysuccinimide. This procedure is depicted in the scheme illustrated in FIG. 11.

Figure 5:
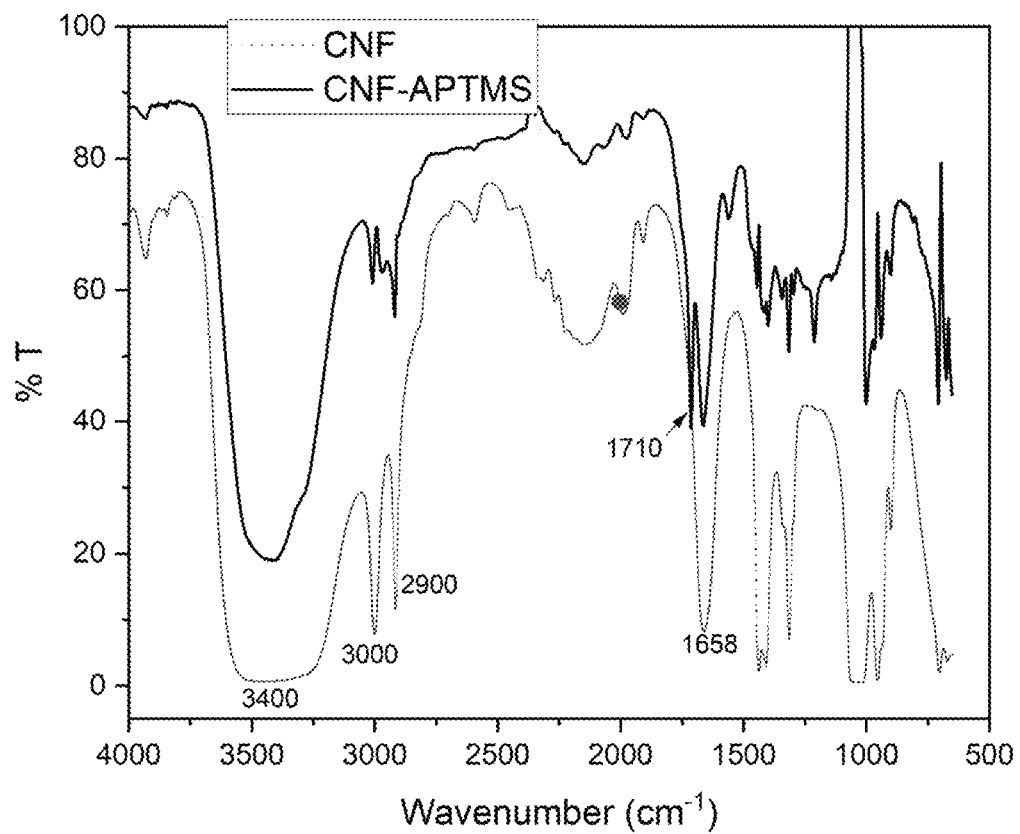
FIG. 5 is an FTIR comparing the spectra of TEMPO oxidized bacterial cellulose with APTMS functionalized bacterial cellulose.

Next, compounds carrying terminal amine functionality, aminopropyltrimethoxy silane (APTMS), were grafted on to the surface activated oxidized CNF molecules through amidation to get functionalized CNF. The reaction was performed at room temperature under stirring for 24 h and in $N_2$ atmosphere. The CNF and the catalysts are to be dispersed well in non-aqueous solvents (DMSO) and get rid of any traces of water so that the siloxane pendants of APTMS could be preserved until it reacts with studied polysiloxane precursors, MTMS, MTES and vinyl silane. This is a sine qua non to form covalent bonds with the siloxane precursor (MTMS/MTES/PVMDMS) in the final step of the process. The chemical evaluation of the modified and unmodified CNF with FTIR analysis is shown in FIG. 5. The carbonyl band at 1658 cm-1 for the TEMPO oxidized bacterial cellulose is reduced and split in two peaks for the APTMS modified CNF. The new carbonyl peak at 1710 cm-1 is a direct indicator of the formation of the amide, evidence of successful functionalization of the CNF by APTMS.

To fabricate cellulose aerogel crosslinked by polysiloxane, a two-step sol-gel process composed of hydrolysis under acidic conditions and polycondensation under basic conditions in a liquid surfactant produces a homogeneous pore structure based on cross-linked nanosized colloidal particles. Large cellulose aerogel was produced using APTES-functionalized cellulose nanofibers crosslinked by the polycondensation reactions of MTMS and APTMS silanes.

Figure 12:
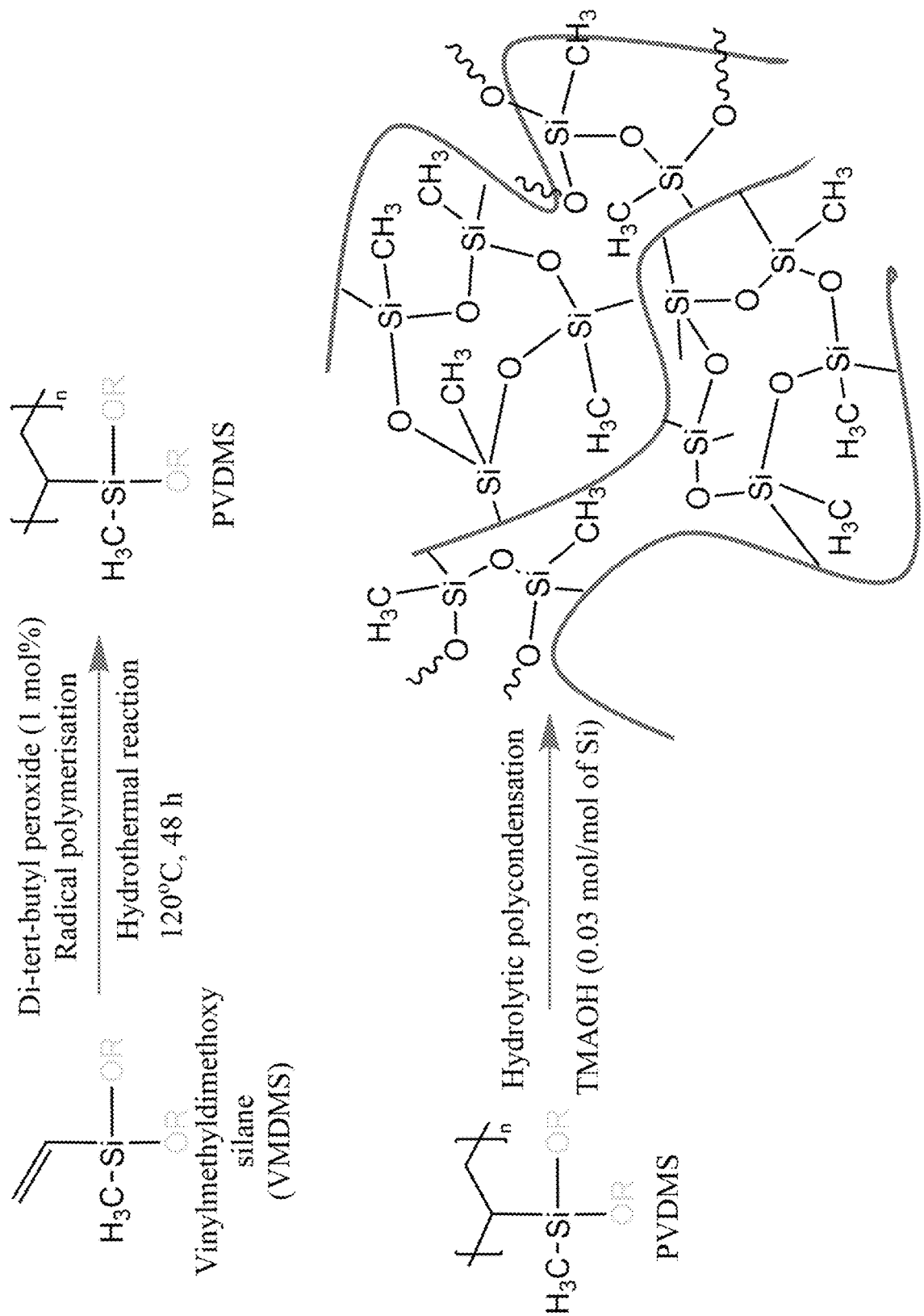
FIG. 12 illustrates an example of a method of preparing a xerogels in accordance with at least one embodiment of the disclosure.

One example of the disclosed xerogels can be prepared by the procedure outlined in Scheme illustrated in FIG. 12 and described below in Example 1.

Example 1

Vinylmethyldimethoxy silane (VMDMS) and di-tert-butyl peroxide (DTBP) (1 mol %) were charged in a hydrothermal reactor. The space above the precursor solution was flushed with nitrogen, and then the reactor was sealed, after which the whole reactor was heated at 120° C. for 48 h followed by cooling naturally at room temperature, affording a transparent and viscous liquid, mainly containing polyvinylmethyldimethoxy silane. To the solution were added benzyl alcohol (4.3 mol/mol Si), $H_2O$ (2 mol/mol Si), cellulose nanofiber grafted with aminopropyl trimethoxysilane CNF-APTMS (1 mol/mol Si) and a base catalyst (trimethylammonium hydroxide) (0.03 mol/mol Si) with specific molar ratio under stirring. After stirring for 5 minutes, the resulting sol was transferred into a mold container, which was then sealed and placed in an oven at 80° C., where the gel formed within 1 hour. The gel was aged at 100° C. for 4 days and subjected to solvent exchange with IPA at 60° C. three times (each 8 hours) to remove the residual chemicals. For ambient drying from IPA, the gel was slowly dried by evaporation at room temperature for 2 to 5 days and at 80° C. for 4 hours to obtain the desired xerogel.

Ambient-dried cellulose aerogels were prepared by varying the cross-linking strategies in order to improve their flexibility, optical transmission and thermal conductivity. One method is to use ethylene-bridged polysiloxane which increases the molecular flexibility of this cross-linking. The other method is based on consecutive processes involving radical polymerization and hydrolytic polycondensation, followed by ultralow-cost, highly scalable, ambient-pressure drying directly from alcohol as a drying medium without any modification or additional solvent exchange. Ambient-dried cellulose aerogels show a high visible-light transmittance of 90% with a visible wavelength range 400-700 nm, an average haze value 3%, and a thermal conductivity lower than 0.01 W/K/m.

Figure 1B:
Figure 1C:
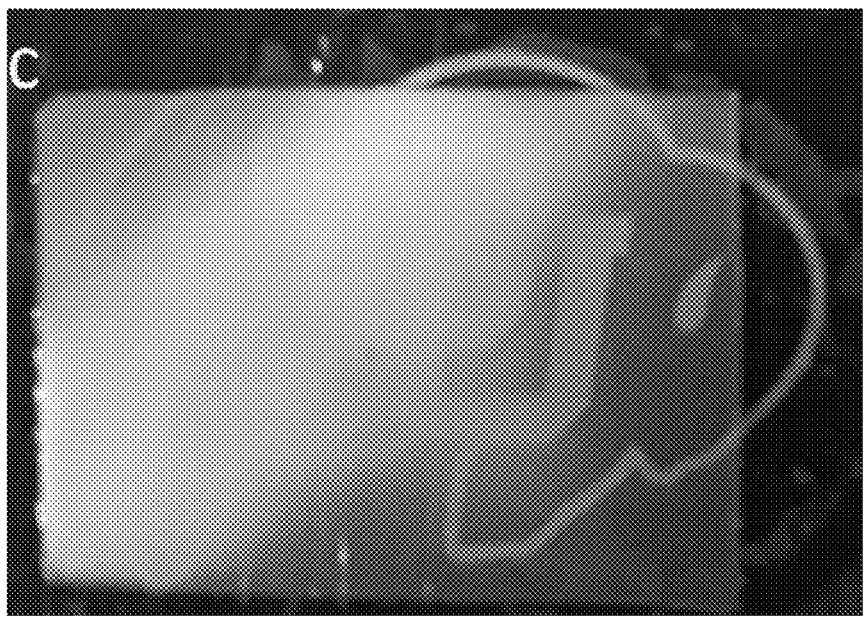
Figure 1D:
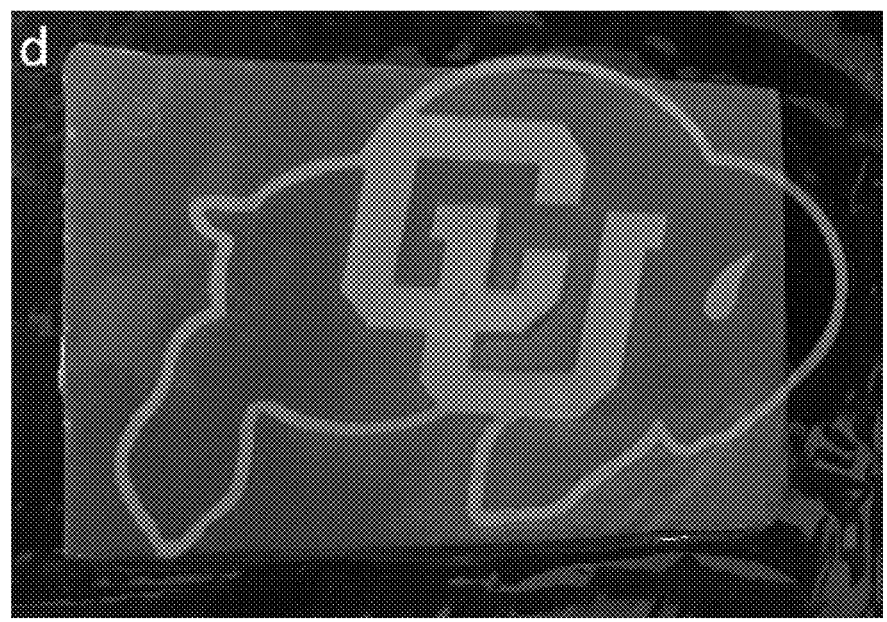
Figure 1E:
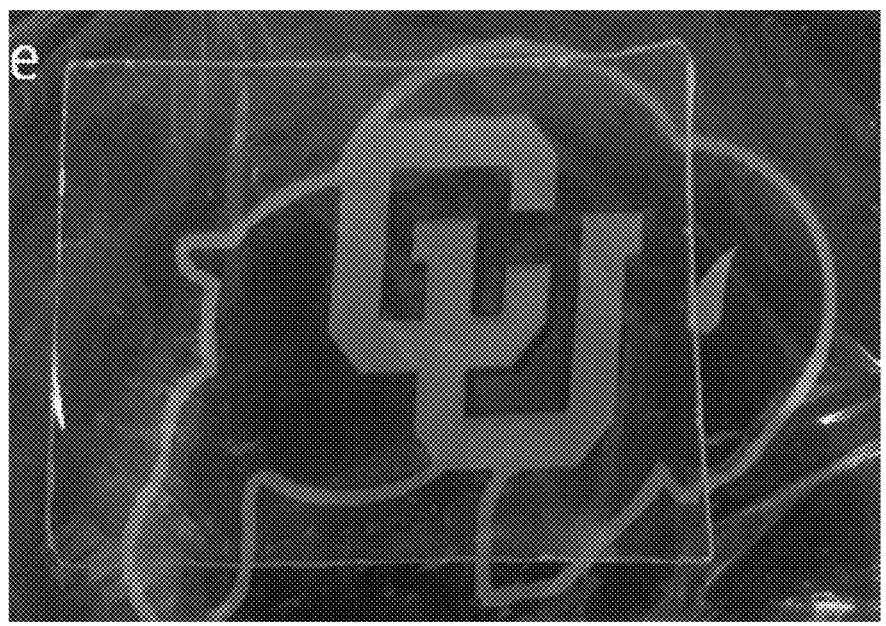

FIGS. 1A-1E depict the transparency characteristics during the course of the xerogel formation described in Example 1. FIG. 1A shows the gel before solvent exchange with IPA, FIG. 1B shows after the alcogel in the first eight hours with IPA, FIG. 1C shows the shrinking behavior of the alcogel during the second 8 hour exchange with IPA, FIG. 1D shows that the alcogel springs back to become transparent in third 8 hour of exchange with IPA, and FIG. 1E shows the final PVMDMS ambient-dried aerogel.

Figure 2:
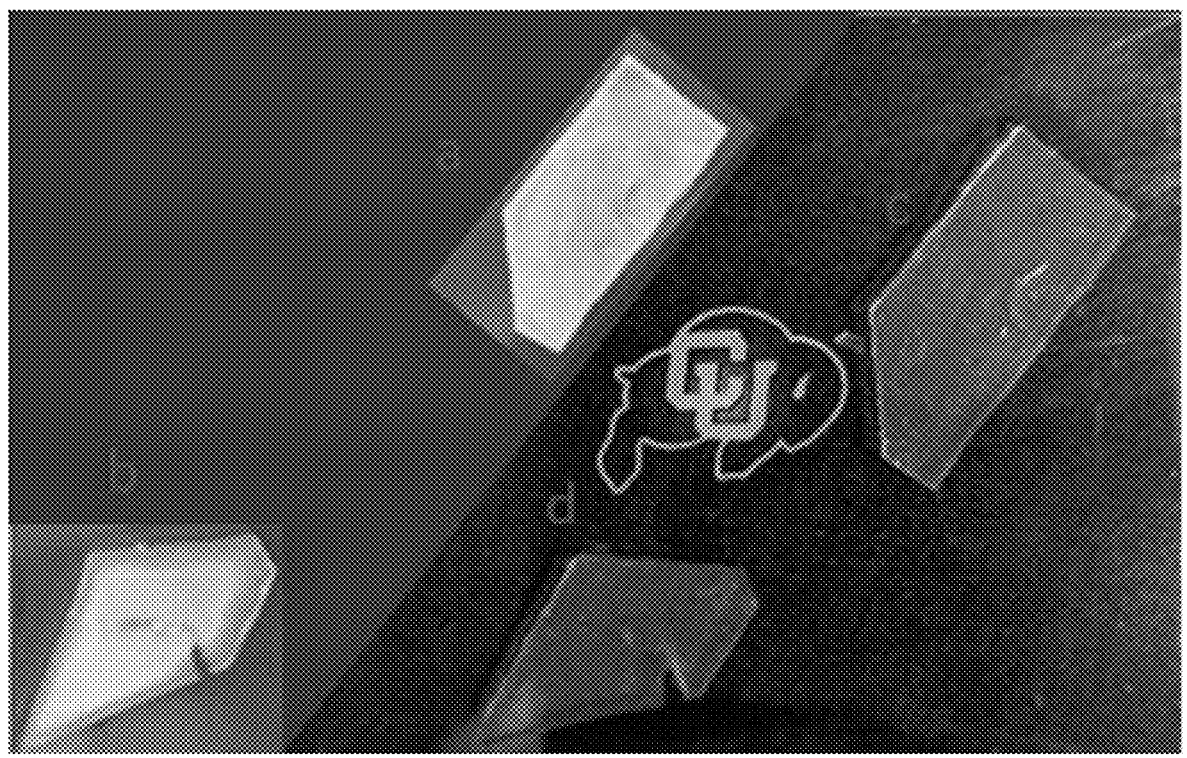
FIG. 2 illustrates that during ambient drying, exemplary alcogels (a) and (b) shrinks and become white. Once dried, they spring back to their original size and are transparent (c and d).

Upon ambient pressure drying, wet gels with IPA undergo large temporary linear shrinkages of around 21% due to the capillary force exerted on the entire gel skeletons and then spring back to nearly their original size, resulting from their elastic molecular structure with abundant methyl groups and aliphatic hydrocarbon chains and few —OH groups. Without wishing to be limited by theory, it is thought that this spring-back phenomenon is due to the flexible skeleton that is folded inward toward the pores during compression, which remains folded in the pores just after the force is removed, then gradually and partially springs back at room temperature, continuing to spring back due to the repulsion and relaxation of the methyl- and aliphatic hydrocarbon chain-rich network during heat treatment. Crack-free large xerogels were obtained via the CNF-APTMS/PVMDMS combination. Since they are obtained by ambient drying without any additional solvent, and processing time, the time, energy and cost savings to the formulator desiring the disclosed ambient-dried aerogels is greatly reduced. FIG. 2 illustrates that during ambient drying, alcogels a and b shrinks and become white. Once dried, the gels spring back to their original size and are transparent (c and d).

The disclosed process can be scaled up to produce larger quantities of aerogels as described in Example 2.

Example 2

Figure 13:
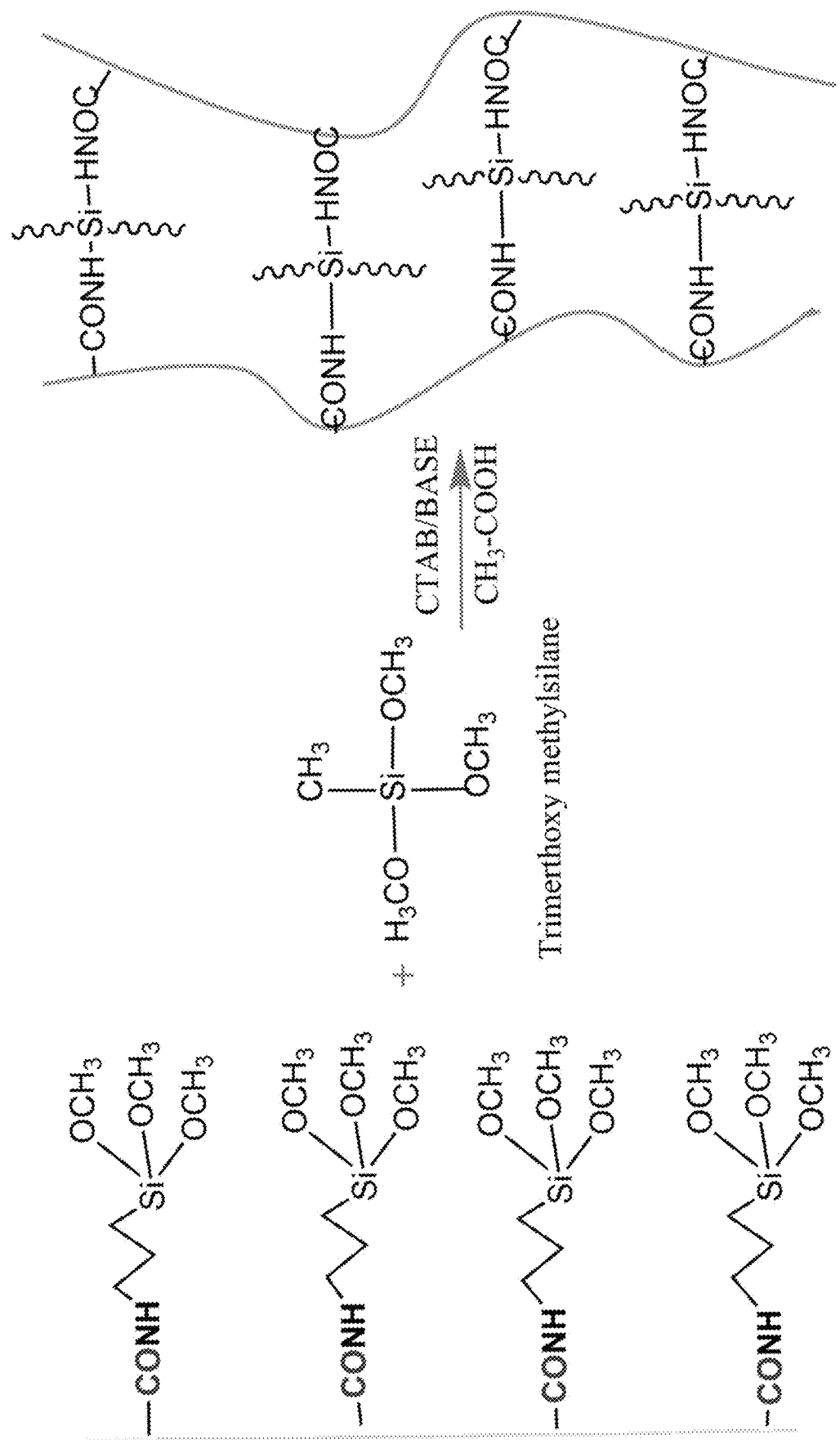
FIG. 13 illustrates proposed reaction mechanism in accordance with at least one example of the disclosure.

200 mg CTAB and 1.5 g urea were dissolved in 5 mL water until it gives a clear solution. Then 1 mL MTMS and 28.7 μL 100 times diluted glacial acetic acid were added to this mixture and stirred for 30 minutes. Finally added APTMS functionalized CNF (0.02 mg/g of Si) into this mixture and continue stirring for 30 minutes at the room temperature. Inject the solution into the mold and seal it well. Keep the entire mold in the oven at 60° C. until it forms a gel, which usually takes 12 h to 24 h. Occasional shaking during the gelation is recommended to remove the generated air bubbles in the gel. After forming the gel, transfer the mold into the water bath at 60° C. for the next 72 hours. After gelation and aging process, carefully remove the gel from the mold with gentle and utmost care for getting a hydrogel without any breaking. The chemical reaction and polycondensation occur between the siloxane precursor and added CNF-APTMS are clearly depicted with proposed reaction mechanism which is shown in the scheme illustrated in FIG. 13.

The CNF acts as a bridging molecule which induces strength and flexibility to the resultant polysiloxane which is advantageous for the preparation of rollable and foldable aerogel and xerogel specifically for the window application.

Figures 6A, 6B, 6C:
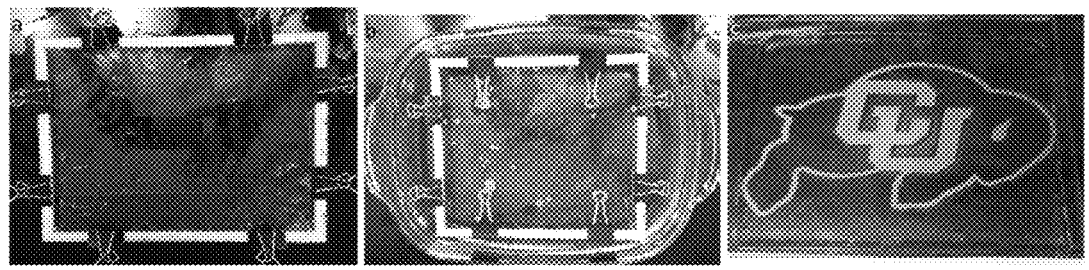
FIGS. 6A-6F depict the fabrication of MTMS/CNF-APTMS large aerogels with glass molds.
Figures 6D, 6E, 6F:
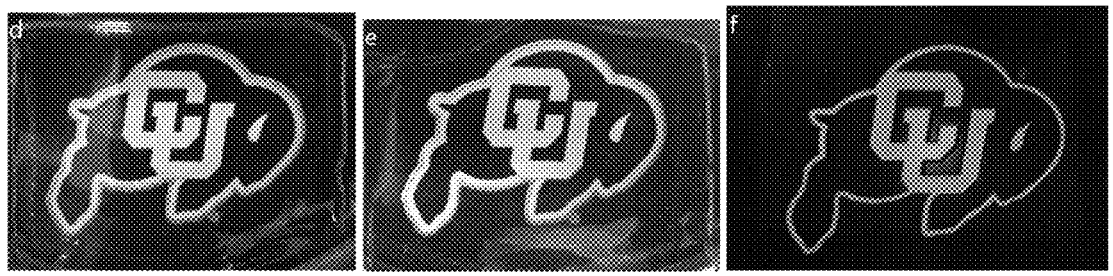

FIGS. 6A-6F depict the fabrication of MTMS/CNF-APTMS large aerogels with glass molds. FIG. 6A shows the mold for the polycondensation reaction chamber made of glass, FIG. 6B the hydrogel fabrication setup in water bath heating, FIG. 6C the hydrogel in DI water, FIG. 6D the alcogel in water/isopropanol, FIG. 6E the alcogel in isopropanol and FIG. 6F shows the final aerogel.

The custom-made molds were fabricated with soda lime glasses and silicone rubber spacers with thickness 3.2 mm. The molds are sealed tightly with epoxy gum in addition to metal clips to hold them together. The mold was kept in water bath for final aging at 60° C. for 72 hours (FIG. 6B). The hydrogel removed after aging were treated first with DI water (FIG. 6C) followed by water/isopropanol (IPA) mixture (FIG. 6D) and finally IPA (FIG. 6E). FIG. 6F depicts the transparent aerogel prepared with 0.02 wt % of CNF-APTMS (visible transmittance >99% and haze <3%).

The next step in the disclosed process is the solvent exchange of the gel into isopropanol.
For that purpose, the entire base and other components (unreacted chemicals, urea, CTAB and water) were removed with successive washing with water, water:IPA mixture (50:50), and finally the gel is stored in pure IPA. It typically takes several days to finish the entire solvent exchange and washing out of extra components. The room temperature is preserved during this whole solvent exchange process. Finally, the gel in IPA dried with critical point dryer (CPD) which was working with liquid $CO_2$. Carefully transfer the 6-inch alcogel in IPA into the CPD chamber with thin 6-inch glass slides. Spacers are placed in between each alcogel. The samples were immersed in ethanol at CPD chamber. The spacers should be thicker than the aerogel to make sure that the top glass will not touch the aerogel. The spacers of 5 mm were used so that each sample could get an additional free space of 2 mm (3 mm sample) in between each of them and put an additional glass on the top of final alcogel sample. The spacers can prevent the ethanol being trapped between the CPD and glass and easy flowing of liquid CO2 during final drying process. It typically takes 6-10 hours to finish the entire CPD process which depend on the thickness of the alcogel and number of samples in the chamber.

Figures 7A, 7B, 7C:
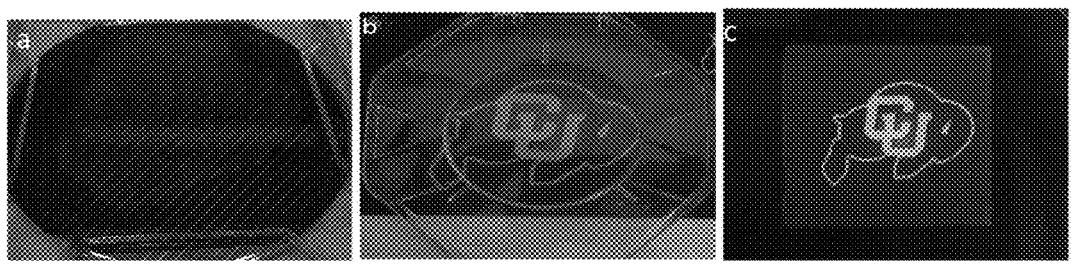
FIGS. 7A-7C represent the large-scale production samples of CNF-APTMS/MTMS aerogel with a 6.5 inch diameter.

FIGS. 7A-7C represent the large-scale production samples of CNF-APTMS/MTMS aerogel with 6.5 inch diameter. As depicted in FIGS. 7A and 7B they are transparent with 1.5 mm and 3 mm thickness with 99% visible transmittance and 2% and 3% respectively haze values as mentioned above. The CNF-APTMS content in these samples are (<0.02 wt %) which reduces the flexibility.

Aerogels made of high percentage CNF-APTMS (0.2 wt %) provides more flexibility (FIG. 7C). The transmittance and haze measurements of this aerogel is described in FIG. 8.

Figure 8:
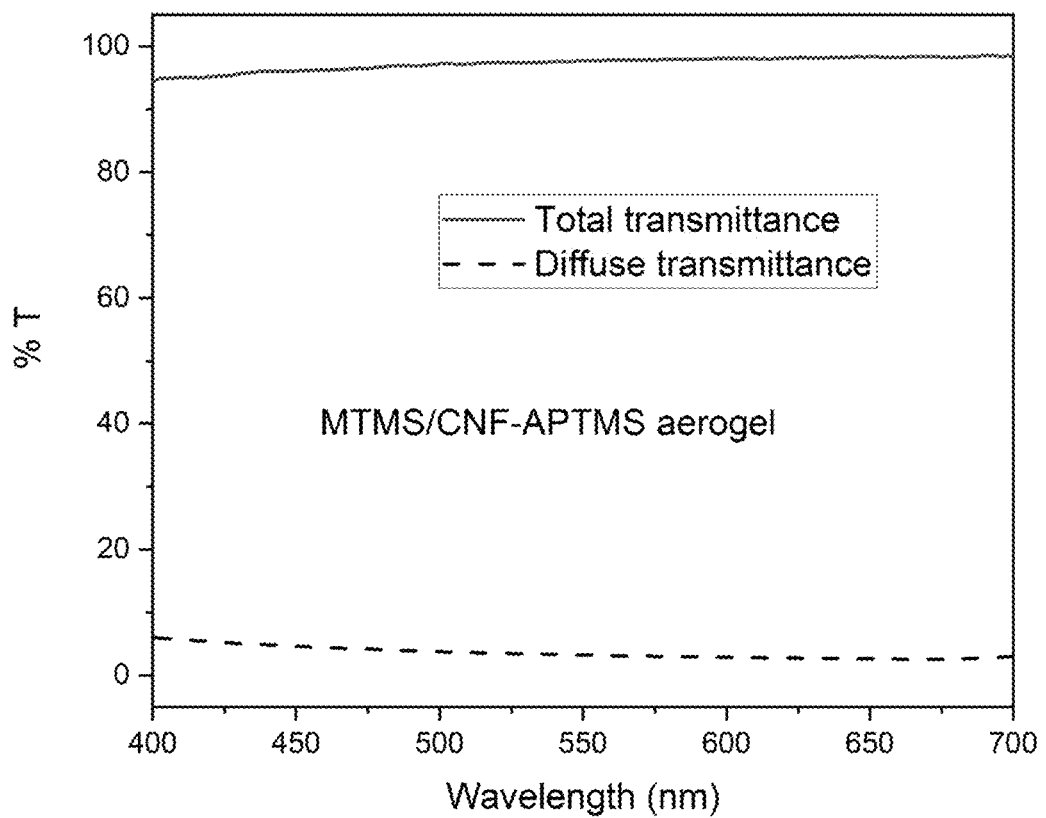
FIG. 8 depicts the transmittance and haze measurements of a disclosed aerogel.
Figure 9A:
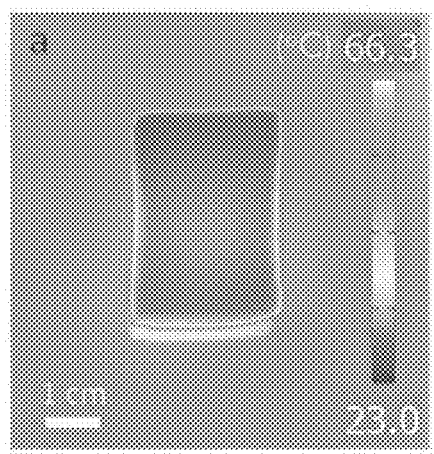
FIGS. 9A and 9B are IR images of a cellulose aerogel on the top of hot (FIG. 9A) and cold surface (FIG. 9B).
Figure 9B:
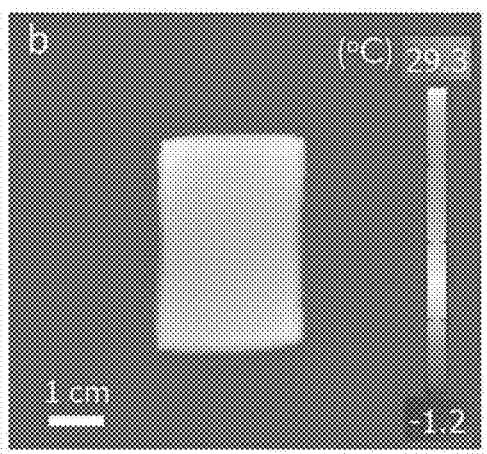

CNF aerogel shows a high visible-light transmittance of 99% with a visible wavelength range 400-700 nm and an average haze value 2% (FIG. 8). These values are worthily commendable since we are applying its highest concentration beyond 0.2 wt % of its dry weight. In order to obtain transparent aerogels, we employed and optimized an acid-base sol-gel reaction in a liquid surfactant-based solution, so as to suppress phase separation between hydrophobic MTMS condensates and polar solvents of water and DMSO. Moreover, the size of the CNF is much reduced to 2 nm to reduce the traces of scattering due the bulky fibers and eventually much flexible aerogel The aerogel has a low thermal conductivity of 11 mW/K/m and the thermal conductance is less than 7.3 $W/K/m^2$. The infrared images show the excellent thermal insulation of aerogel on the surface of hotplate and the ice-water. FIGS. 9A and 9B are IR images of a cellulose aerogel on the top of hot (FIG. 9A) and cold surface (FIG. 9B), showing the excellent thermally insulating property of cellulose aerogel. The cellulose aerogel is also very flexible by nature. It could be easily and will spring back after removing the load.

Figure 10A:
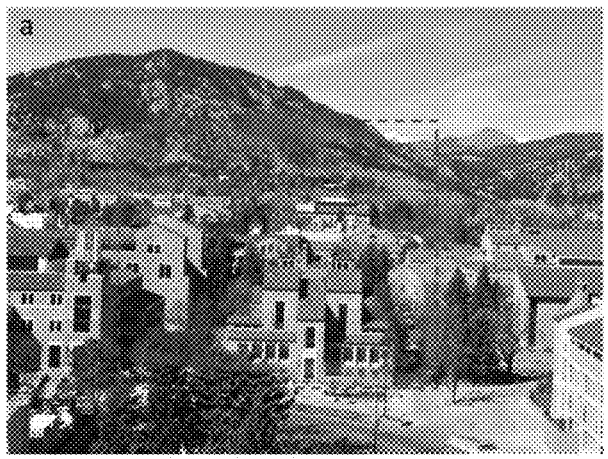
FIG. 10A is a photograph taken through a pane of aerogel (dotted red square) and FIG. 10B is the IR image of the same picture showing the thermally insulating properties of the aerogel.
Figure 10B:
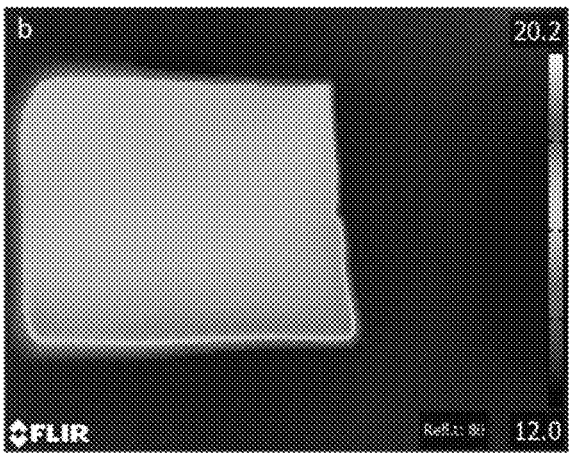

The disclosed aerogels are suitable for use as or add-ons for glass in conventional windows. FIG. 10A is a photograph taken through a pane of aerogel (dotted red square). The dimensions are 6.5 inch in diagonal and 2.5 mm thick. FIG. 10B is the IR image of the same picture showing the thermally insulating properties of the aerogel.

Free standing aerogels should be handled with care which may not be compatible with a pilot scale production. In addition, storage of aerogels can also be tricky as they would stick to each other if stacked.

In some cases, it may be desirable to directly form the aerogel (such as any of the aerogels described herein) on a substrate, such as a pane of glass. In some cases, maximizing the reaction between hydrolyzed MTMS and silanol from the surface of the glass is desired to obtain a strong anchoring of the hydrogel. The idea is that the gel will remain attached to the glass during all the processes, and will be sold with that same substrate.

Figure 14:
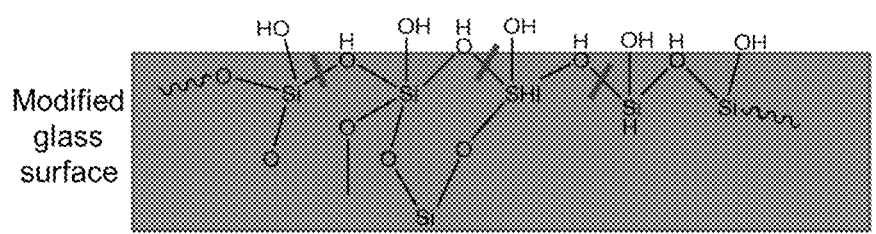
FIG. 14 illustrates silanol on the surface of our substrate.

There are different ways to modify the density of silanol on glass. One way is to use piranha solution to treat substrates. Piranha is a dangerous chemical obtained by mixing sulfuric acid with hydrogen peroxide. Even though it can be unstable, it is used to clean wafer, resins in microelectronics. After that treatment, we expect a higher density of silanol on the surface of our substrate, as depicted in FIG. 14. One of the great things about that modification is that it does not affect further steps. The gels are made the exact same way in the lab whether the glass is modified or not.

Figure 15:
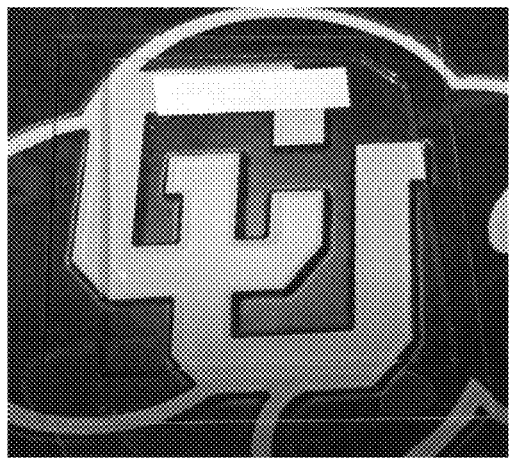
FIG. 15 illustrates gel attached to a modified glass substrate in accordance with at least one embodiment of the disclosure.
Figure 15:
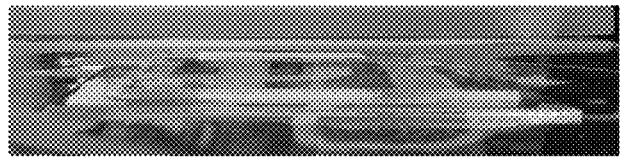
Figure 15:

After curing the hydrogel, the gel can be unmolded. At that step we see that the gel is attached to the modified glass substrate (FIG. 15). The gel is then solvent exchanged to IPA before being dried in a CPD chamber. To allow the stacking of several samples inside the CPD chamber, the alcogel on the glass substrate can be protected by an aluminum casing. Finally, the air film is dried on glass.

While piranha use is quite common in a chemistry laboratory, it may not be the best choice in some circumstances because it is relatively unstable, explosive. A commercial solution of piranha that is stable may be used. Or, a concentrated solution of KOH or other chemical treatment may be used.

Plasma treatments are used for treating surfaces of various materials prior to any coating, printing or adhesion. Treatment with plasma removes any foreign contaminants present on the surface of a material making it more suitable for further processing. If used under certain conditions, it can also implant some foreign ions in the substrate to modify the surface function. This treatment not only work on glass, but can be used on polymer films for the retrofit application. The plasma treatment can be used for making a glass substrate and cellophane film surfaces more hydrophilic and eventually getting a better adhesion with the hydrogel.

Last, a primer layer comprising a siloxane or silica precursor can be deposited on the substrate via physical or chemical deposition. This can be done using typical low-E coaters present on industrial glass production lines.

Growing a gel directly on a substrate not only helps the streamlining of production using existing equipment. The direct bond at the glass/gel interface can prevent shrinkage and cracking of the gel (during gelification, and drying). It also allows cutting the gel using regular glass cutting technologies.

The present invention has been described above with reference to a number of exemplary embodiments and examples. It should be appreciated that the particular embodiments shown and described herein are illustrative of the preferred embodiments of the invention and its best mode, and are not intended to limit the scope of the invention. For example, unless otherwise noted, steps can be performed in any order and some steps may be performed simultaneously. It will be recognized that changes and modifications may be made to the embodiments described herein without departing from the scope of the present invention. These and other changes or modifications are intended to be included within the scope of the present invention.

What is claimed is:

1. A transparent and flexible cellulose nanofiber-polysiloxane composite aerogel comprising:
   cellulose nanofibers having a diameter between about 4 and about 10 nm,
   wherein the transparent and flexible cellulose nanofiber-polysiloxane composite aerogel is formed using a polysiloxane precursor and a surface modifying agent comprising a compound comprising an amine functional group,
   wherein the cellulose nanofibers are crosslinked via a polysiloxane network comprising a siloxane bond derived from the polysiloxane precursor, and
   wherein the flexible cellulose nanofiber-polysiloxane composite aerogel is rollable and foldable.

2. The composite aerogel of claim 1 having a thickness from about 1 µm to about 10 cm.

3. The composite aerogel of claim 1 having an electromagnetic transmission of from about 25% to about 100% for light wavelengths between about 400 nm and about 700 nm.

4. The composite aerogel of claim 1 having a thermal conductivity of from about $10^{-3}$ W/(m·K) to about 10 W/(m·K).

5. The composite aerogel of claim 1, wherein the cellulose nanofibers are derived from bacterial cellulose.

6. The composite aerogel of claim 1, wherein the cellulose nanofibers are functionalized with siloxane pendants derived from the surface modifying agent.

7. A film comprising the composite aerogel of claim 1.

* * * * *